US012000968B2

United States Patent
Martins

(10) Patent No.: US 12,000,968 B2
(45) Date of Patent: Jun. 4, 2024

(54) 2D ULTRASOUND IMAGING WITH PULSED WAVE DOPPLER OR COLOR FLOW IMAGING

(71) Applicant: B-K Medical Aps, Herlev (DK)

(72) Inventor: Bo Martins, Rodovre (DK)

(73) Assignee: B-K MEDICAL APS, Herlev (DK)

( * ) Notice: Subject to any disclaimer, the term of this patent is extended or adjusted under 35 U.S.C. 154(b) by 688 days.

(21) Appl. No.: 16/080,366

(22) PCT Filed: Feb. 29, 2016

(86) PCT No.: PCT/IB2016/051110
§ 371 (c)(1),
(2) Date: Aug. 28, 2018

(87) PCT Pub. No.: WO2017/149350
PCT Pub. Date: Sep. 8, 2017

(65) Prior Publication Data
US 2019/0049567 A1    Feb. 14, 2019

(51) Int. Cl.
*G01S 7/52* (2006.01)
*A61B 8/00* (2006.01)
*G01S 15/89* (2006.01)

(52) U.S. Cl.
CPC ............ *G01S 7/52073* (2013.01); *A61B 8/46* (2013.01); *G01S 7/52066* (2013.01); *G01S 15/8984* (2013.01); *G01S 15/8986* (2013.01)

(58) Field of Classification Search
None
See application file for complete search history.

(56) References Cited

U.S. PATENT DOCUMENTS 6,048,314 A * 4/2000 Nikom ............... A61B 5/02007
600/443
6,068,598 A    5/2000 Pan et al.
(Continued)

FOREIGN PATENT DOCUMENTS

EP    1152364 A2 * 11/2001 ............... A61B 8/06
EP    1152364 A2    11/2001

OTHER PUBLICATIONS

International Search Report for PCT/IB2016/051110 published as WO2017149350 dated Sep. 8, 2017.

*Primary Examiner* — Patrick Fernandes
*Assistant Examiner* — Marjan Saboktakin
(74) *Attorney, Agent, or Firm* — Daugherty & Del Zoppo, Co. LPA

(57) ABSTRACT

An ultrasound imaging system includes receive circuitry (110) configured to receive electrical signals from ultrasound transducer elements wherein the electrical signals are indicative of sensed ultrasound echo signals. The system further includes an image process (114) configured to process the electrical signals and generate a 2-D image. The system further includes a vessel wall identifier (116) configured to identify at least a proximal wall and a distal wall of a vessel in the B-mode image from the B-image employing a signal mirroring technique. The system further includes a rendering engine (124) configured to display the 2-D image on a display (126) with graphical indicia corresponding to the identified proximal wall and distal wall superimposed over the vessel in the 2-D image.

20 Claims, 8 Drawing Sheets

(56) References Cited

U.S. PATENT DOCUMENTS

| | | | |
|---|---|---|---|
| 2003/0125624 A1* | 7/2003 | Shiki | G01S 15/8984 |
| | | | 600/443 |
| 2007/0123777 A1* | 5/2007 | Watanabe | A61B 5/02007 |
| | | | 600/437 |
| 2014/0213905 A1 | 7/2014 | Saad et al. | |
| 2014/0276072 A1* | 9/2014 | Martins | A61B 8/488 |
| | | | 600/454 |

* cited by examiner

2D ULTRASOUND IMAGING WITH PULSED WAVE DOPPLER OR COLOR FLOW IMAGING

RELATED APPLICATION

This application is a national filing of PCT application Serial No. PCT/IB2016/051110, filed Feb. 29, 2016, published as WO2017/149350 on Sep. 8, 2017. This application claims priority to PCT application Serial No. PCT/IB2016/051110, published as WO2017/149350 on Sep. 8, 2017.

TECHNICAL FIELD

The following generally relates to ultrasound and more particularly to two-dimensional (2-D) ultrasound imaging with pulsed wave Doppler or color flow imaging.

BACKGROUND

Doppler ultrasound is used to measure velocity of flow of blood cells inside a sub-portion of a blood vessel defined by a Doppler gate. The Doppler gate is manually placed using B-mode imaging in connection with color flow mapping (CFM). For this, the transducer is positioned so that the B-mode image shows the blood vessel of interest. A CFM is superimposed there over. The CFM shows relative blood flow direction, determined based on a phase shift between transmitted and returning frequencies, with positive shifts indicating blood is moving away from the transducer, and negative shifts indicating blood is moving towards the transducer. The Doppler gate is placed along the line of insonation about a cross section of the vessel, using the CFM as a guide.

Velocity is calculated for the sample volume from the Doppler frequency shift according to EQUATION 1:

$$V = \frac{C}{2 f_o \cos \psi} \Delta f. \quad \text{EQUATION 1}$$

where V represents flow velocity, $\Delta f$ represents the Doppler shift, $f_o$ represents the original transmit frequency, C represents the speed of sound in soft tissue, and $\psi$ represents the angle between the beam and the blood flow. From EQUATION 1, V is inversely proportional to $\cos \psi$, and the V approaches zero (0) as $\psi$ approaches ninety degrees (90°) (i.e., $\cos 90 = 0$). An angle of approximately forty-five degrees (45°) to sixty degrees (60°) has been used to obtain velocity estimations. The beam is electronically steered to this range by adjusting the transmit and/or receive profile of the transducer elements, or mechanically steered. Electronic steering has been limited to −20 degrees, 0 degrees, or +20 degrees, and angle correction is applied.

U.S. Pat. No. 9,247,927 describes an approach in which vector flow imaging (VFI) is used to identify a position of peak blood flow velocity and automatically determine a Doppler steering angle, compute a direction of the flow at the Doppler gate, and apply Doppler angle correction. In '927, VFI is also used to adaptively adjust the Doppler sample volume size, invert the Doppler spectrum if needed, and/or automatically determine and display in real time an indicator for the diameter of the vessel within the Doppler gate and estimate a volume flow rate based thereon. However, with VFI the framerate is often slower than with regular color flow imaging and penetration is limited. Furthermore, the vessel diameter and hence the volume flow rate may be inaccurate since VFI is sensitive to color gain.

SUMMARY

Aspects of the application address the above matters, and others.

In one aspect, an ultrasound imaging system includes receive circuitry configured to receive electrical signals from ultrasound transducer elements wherein the electrical signals are indicative of sensed ultrasound echo signals. The system further includes an image process configured to process the electrical signals and generate a 2-D image. The system further includes a vessel wall identifier configured to identify at least a proximal wall and a distal wall of a vessel in the B-mode image from the B-image employing a signal mirroring technique. The system further includes a rendering engine configured to display the 2-D image on a display with graphical indicia corresponding to the identified proximal wall and distal wall superimposed over the vessel in the 2-D image.

In another aspect, a method includes generating a B-mode image from ultrasound data, identifying a vessel wall of a predetermined vessel in the B-mode image using a signal mirroring technique, and visually presenting the B-mode image with an overlay of an outline of the identified vessel wall.

In another aspect, an apparatus includes a memory configured to store a signal mirroring algorithm, a processor configured to process the electrical signals indicative of sensed ultrasound echo signals and generate a 2-D image, determine a proximal wall and a distal wall of a vessel using the signal mirroring algorithm, and a display (126) configured to display the 2-D image with the wall of the vessel visually identified therein.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
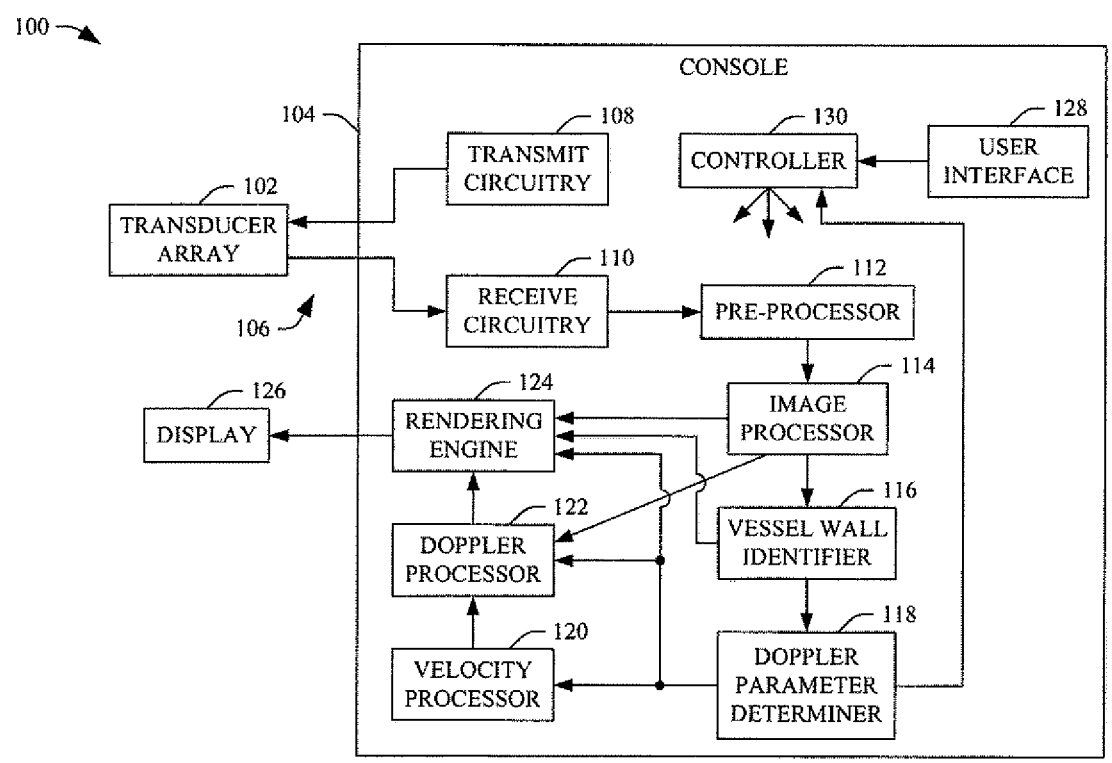
FIG. 1 schematically illustrates an example ultrasound imaging system with a vessel wall identifier configured to identify a vessel wall from a B-mode image.

FIG. 1 schematically illustrates an example ultrasound imaging system 100. The system 100 includes a transducer array 102 and a console 104. The transducer array 102 and the console 104 communicate with each over a communications channel 106, which may include a hardwired and/or wireless communications channel. It is to be appreciated that the ultrasound imaging system 100 may be a hand held, a portable (e.g., on a cart with wheels), and/or a stationary system, and/or the console 104 can be a separate computer.

The transducer array 102 converts an electrical signal to an ultrasound pressure field, and vice versa. More specifically, the transducer array 102 includes an array of multiple transducer elements that are configured to transmit ultrasound signals and receive echo signals. Examples of suitable arrays include 32, 128, 192, and/or other elements arrays, including square and rectangular arrays. The array can be linear, curved, and/or otherwise shaped, fully populated, sparse and/or a combination thereof, etc.

Transmit circuitry 108 generates a set of pulses that are conveyed to the transducer array 102, which excites a set of the transducer elements of the transducer array 102, causing the excited transducer elements to transmit, at predetermined transmit frequency, ultrasound signals into an examination or scan field of view. Receive circuitry 110 receives electrical signals from the transducer array 102 indicative of received echo signals, which are generated in response to the transmitted ultrasound signals traversing structure such as blood cells flowing in a tissue of interest.

A pre-processor 112 processes the received electrical signals. Suitable processing includes amplifying the signals, digitizing the signals, applying time delays and weights and summing the delayed and weighted signals, echo-cancelling, wall-filtering, base banding, averaging and decimating, lowering speckle, improving specular reflector delineation, filtering (e.g., FIR, IIR, etc.), envelope detection, compressing, and/or other pre-processing. An image processor 114 processes the data and generates one or more two-dimensional (2-D) images. In the illustrated embodiment, the image processor 122 at least generates a B-mode image.

A vessel wall identifier 116 identifies a sub-portion of a vessel wall (e.g., proximal and distal wall portions) in the B mode image, e.g., for the location of the Doppler gate. In one instance, the vessel wall identifier 116 employs a tissue mirroring approach to identify the sub-portion. However, other approaches are contemplated herein. Generally, tissue signal close to a proximal vessel wall (i.e., the vessel wall closest to the transducer) mirrors proximal tissue signal in the vessel wall, which acts as a strong reflector. This is described in connection with FIG. 2, which shows a proximal vessel wall (or reflecting boundary) 202, a focusing position 204, and a tissue mirror position 206. A relative magnitude of the envelope data at the reflecting boundary 202 compared to the tissue signal shows a degree of reflectance. Some of a signal reaches the focusing position 204 and reflects back to the mirror position 206 and/or the transducer array 102, some of the signal reflects off the reflecting boundary 202 and reflects back to the mirror position 206 and/or the transducer array 102, and some of the reflecting signal reflects off the mirror position 206 and back towards the reflecting boundary 202.

Figure 2:
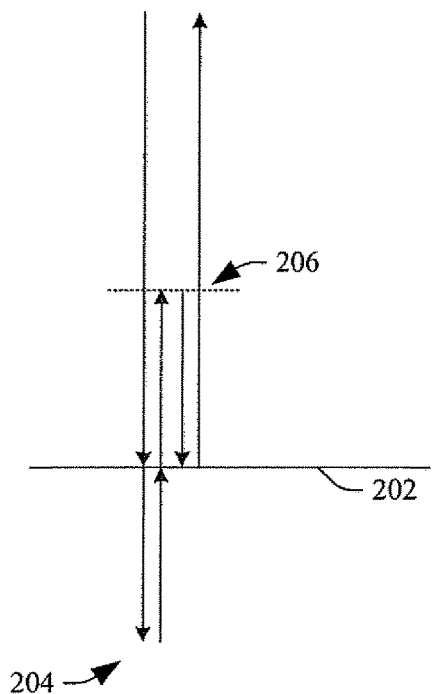
FIG. 2 discusses tissue mirroring between vessel tissue and tissue proximal to the vessel.

A precise orientation of the reflecting boundary 202 is not easily assessed so a location of the mirroring point 206 is not precisely known. When compounding is used there are multiple (e.g., 3 to 5) mirroring points. Spatial compounding is the process of aligning and combing frames of the same structure, which are acquired at different times and at different angles of insonation, to form a single compounded frame. Compounding can be performed after inverse compression of compressed envelope data. The mirroring effect decreases with a distance to the reflecting boundary 202 and it generally is not possible to make out particular features of the proximal image in the signal. FIG. 2 describes a non-limiting approach for identifying the vessel wall by detecting mirroring.

The vessel wall identifier 116, for a predetermined sample length and a predetermined weight length, adds non-compressed envelope values with a first set of weights and subtracts non-compressed envelope data with a second set of weights. The first set of weights and second set of weights are separated by one or more samples. Where the compounded image is axially resampled to 768 samples, a suitable length value is 32, greater or less. The combined effect of the subtraction of weighted signals is a weighted sum of length+1 axial samples, where the last one is the current sample, and the sum of the weights equal zero.

This approach is modified slightly in the very near field as the skin layers have the same appearance as vessel walls. Close to the transducer surface a lower value of length is used and an offset is introduced. In general, the mirroring strength is set equal to the weighted sum divided by the sum of the positive weights, and having an offset subtracted from this number, where the offset is decreased monotonically (e.g. linearly) from some constant value at the probe surface to zero at a specific sample depth. If the computed value is negative, the mirroring strength is set equal to 0.

Figure 3:
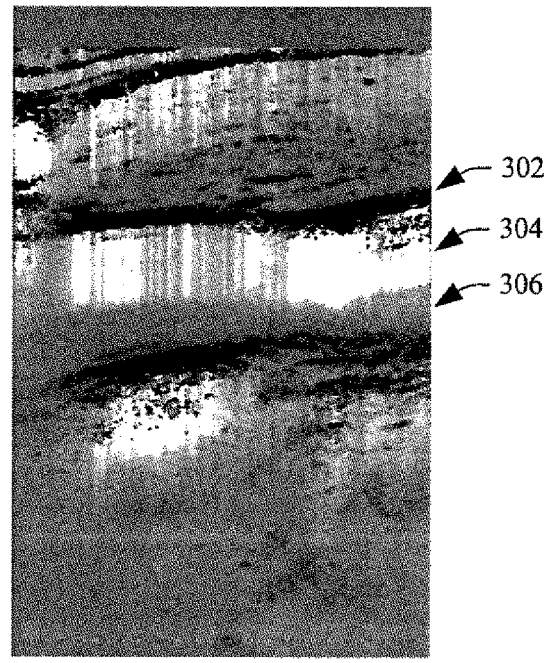
FIG. 3 shows an expected strength of the mirroring signal.
Figure 4:
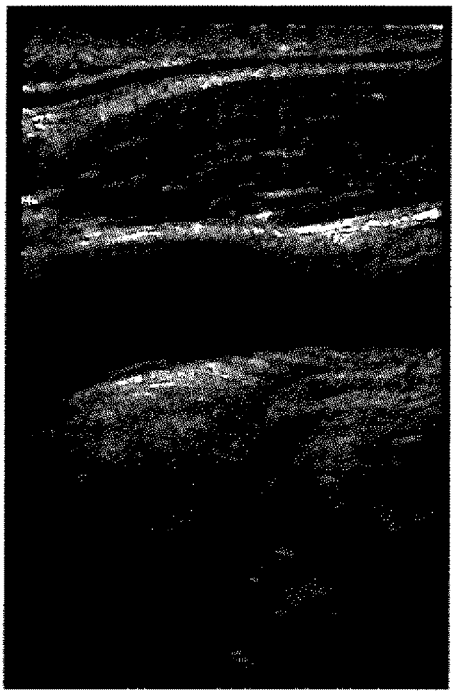
FIG. 4 shows the compressed image.
Figure 5:
FIG. 5 shows a fluid definition mask in which low-echo tissue signal inside the vessel, but not the oblique part, is masked out.

FIG. 3 shows an expected strength of the mirroring signal for a particular case of the common carotid artery where the weights except for the very near field are $-1, -1, \ldots, -1, 32$. In FIG. 3, the offset at depth 0 is 10 and a linear rate of decay of 0.18 is applied. The expected strength is set in relation to the compressed data. The expected strength is large if a dark area 302 is adjacent to a bright area 304 that is adjacent to a less bright area 306. FIG. 4 shows the compressed image, and FIG. 5 shows a fluid definition mask in which low-echo tissue signal inside the vessel, but not the oblique part, is masked out. The fluid definition mask is generated by thresholding of the uncompressed signal minus the computed mirroring strength.

Figure 6:
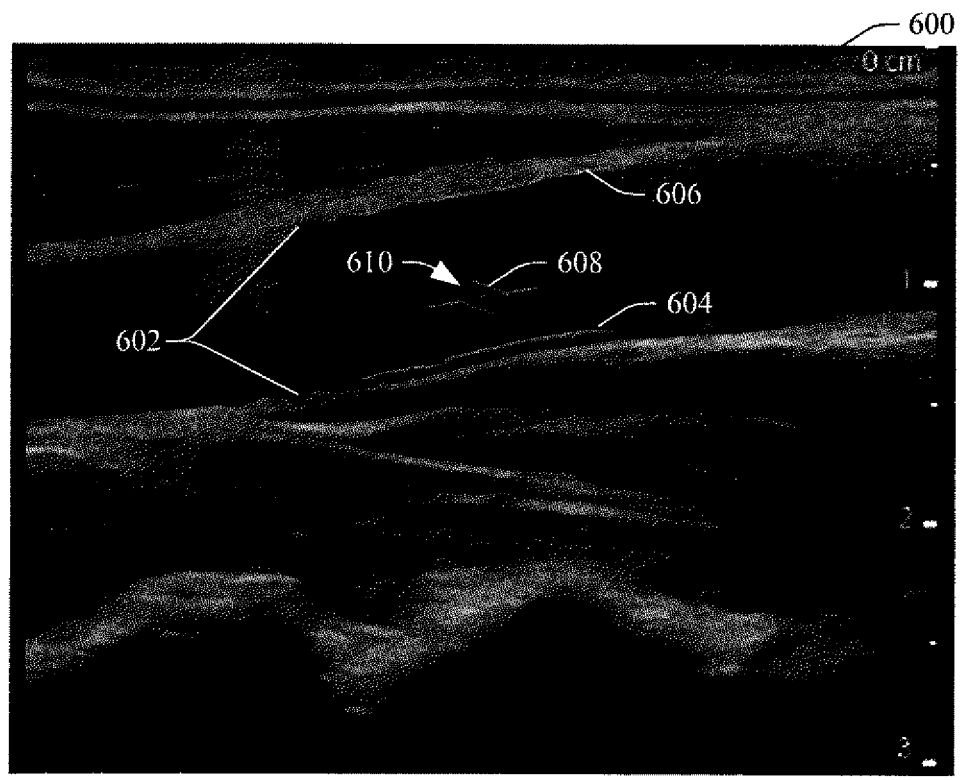
FIG. 6 shows a B-mode image of a vessel with the vessel wall identified therein using graphical indicia.

FIG. 6 shows a B-mode image 600 of a vessel 602, including a proximal vessel wall 604 of the vessel 602 and a distal wall 606 of the vessel 602, and a Doppler gate 608 (defining a sample volume 610) disposed within the vessel 602. The Doppler gate 608 is placed based on VFI, color flow imaging (CFI), and/or an audio signal for determining a position of maximum velocity. In the latter case, angle correction enables continuous angle corrected amplification of the audio signal thereby avoiding wrong conclusions.

Figure 7:
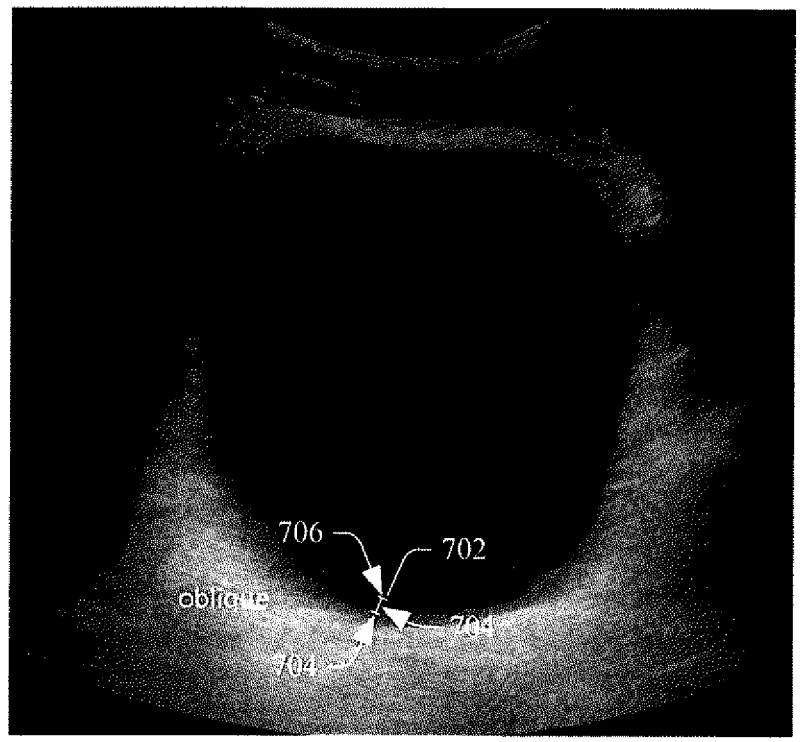
FIG. 7 shows a B-mode image of an estimated wall of a bladder identified therein using graphical indicia.
Figure 8:
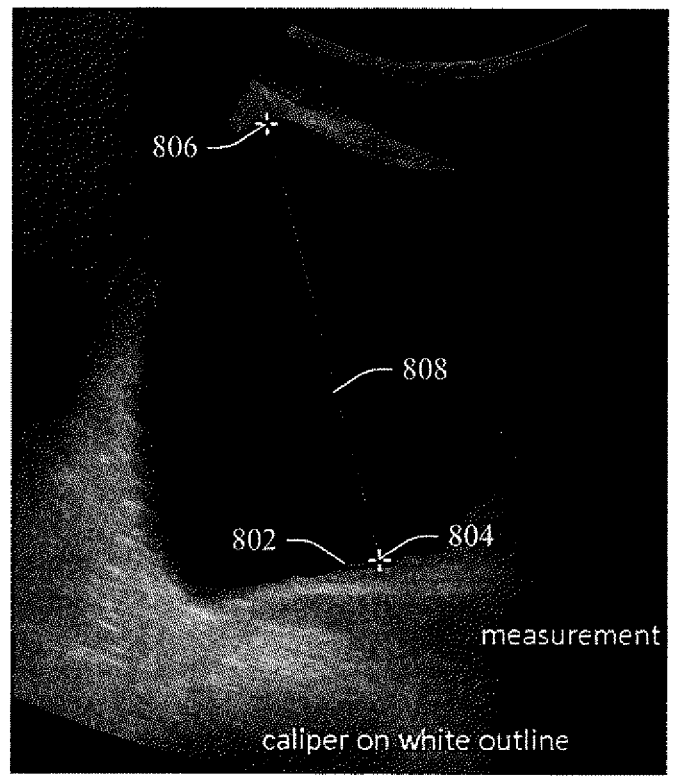
FIG. 8 shows a B-mode image of an estimated wall of a bladder identified therein using graphical indicia and a measurement made therewith.

FIGS. 7 and 8 show graphical representations of estimated walls for a non-Doppler application. In general, the graphical representation of estimated walls can always be shown in the B-mode images (e.g., a continuous overlay), shown on demand, automatically shown based on the active ultrasound mode (e.g., Doppler, measurement, etc.), and/or otherwise shown. For example, in measurement mode, in FIG. 7, a white line 702 indicates a wall of the bladder. From the white line 702, the observer can see that the transducer is not held sufficiently accurate for measurements to be carried out. This can be determined by a distance 704 from the first detected appearance 706 of the posterior (or distal) wall of the bladder and the visually apparent 708 bladder wall. The distance 704 indicates that the imaging plane is not perpendicular to the bladder. Consequently, the image is not good enough on which to make measurements. In contrast, in FIG. 8, a white line 802 indicates the estimated wall, and the observer can see that the transducer is held sufficiently accurate for measurements to be carried out, as a distance from the first detected appearance of the wall and the visually apparent bladder wall is close. A marker 804 is placed on the white line 802; another marker 804 is placed on another wall, and a distance 808 there between is measured.

Returning to FIG. 1, a Doppler parameter determiner 118 determines a flow direction based on at least one of the identified proximal and distal walls. In one instance the Doppler parameter determiner 118 fits a line to each of the vessel walls 604 and/or 606 (FIG. 6) and determines the flow direction to be along a direction of the fitted line(s). In another instance, the Doppler parameter determiner 118 uses only a sub-portion of the identified vessel walls. For example, where the vessel walls are irregular, include curvature, etc. a sub-portion of the vessel walls may provide a more accurate indication of the actual flow direction.

The flow direction can be determined continuously, frame by frame, and/or otherwise, e.g., based on an average of wall locations, a most current location, etc. It is to be appreciated that identifying the proximal and distal walls as described herein and using the identified proximal and distal walls to determine the flow direction reduces the amount of time to determine the flow direction, e.g., relative to VFI and/or reduces the uncertainty in the location of the proximal and distal walls relative to VFI, e.g., at least because VFI which requires several cardiac cycles to determine flow angles, and the measurements might not all be parallel to the proximal and distal walls, which may lead to wall location uncertainty.

The Doppler parameter determiner 118 further determines a suitable Doppler steering angle between the Doppler ultrasound beam direction and the direction of the flow determined based on the identified wall(s). Again, an angle of approximately forty-five degrees (45°) to sixty degrees (60°) has been used to obtain velocity estimations to reduce measurement inaccuracy. Other angles are also contemplated herein. The Doppler parameter determiner 118 can further adjust the Doppler gate sample volume 610 based on the identified the walls 604/606 so that the gate 608 is at the walls 604/606, within the walls 604/606 (FIG. 6), outside of the walls 604/606, and/or a combination thereof. The Doppler parameter determiner 118 can further determine an angle correction.

A velocity processor 120 computes a flow velocity for the Doppler gate based on the output of the Doppler parameter determiner 118, e.g., using EQUATION 1 and/or otherwise. A Doppler processor 122 generates information about the power spectral density of the received blood flow Doppler-shift frequencies, for example, in the form of a 2D spectrogram, which provides the Doppler frequency-shift as a function of time. The Doppler processor 122 generates this information based on the output of the Doppler parameter determiner 118 and the B-mode image.

Figure 9:
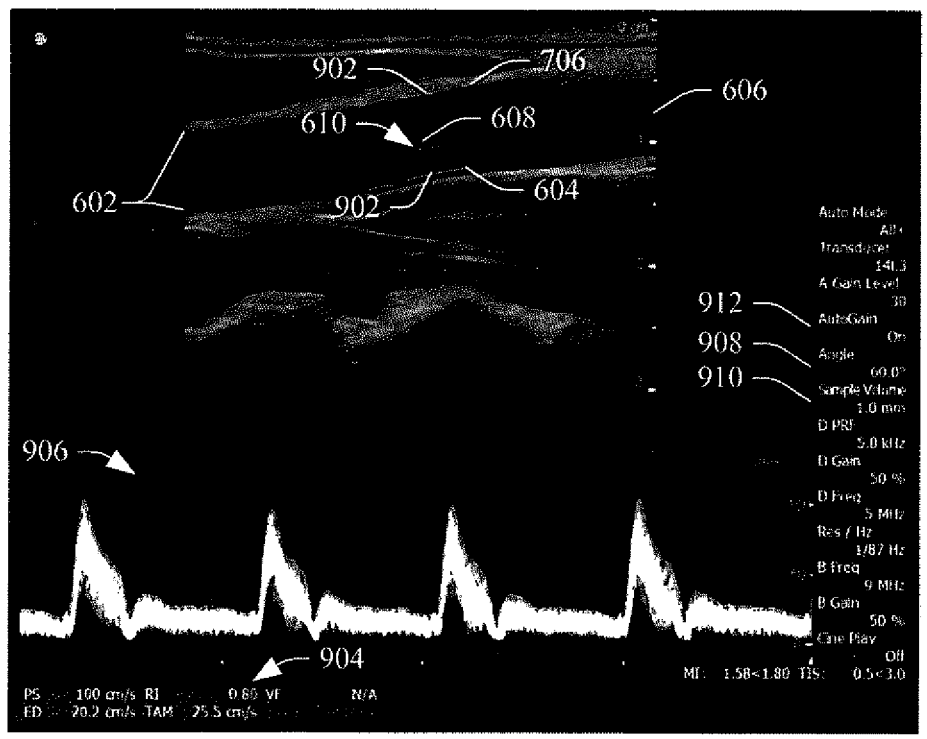
FIG. 9 shows an example graphical user interface displaying a B-mode image, graphical indicia indicating the identified vessel wall, and other information.
Figure 10:
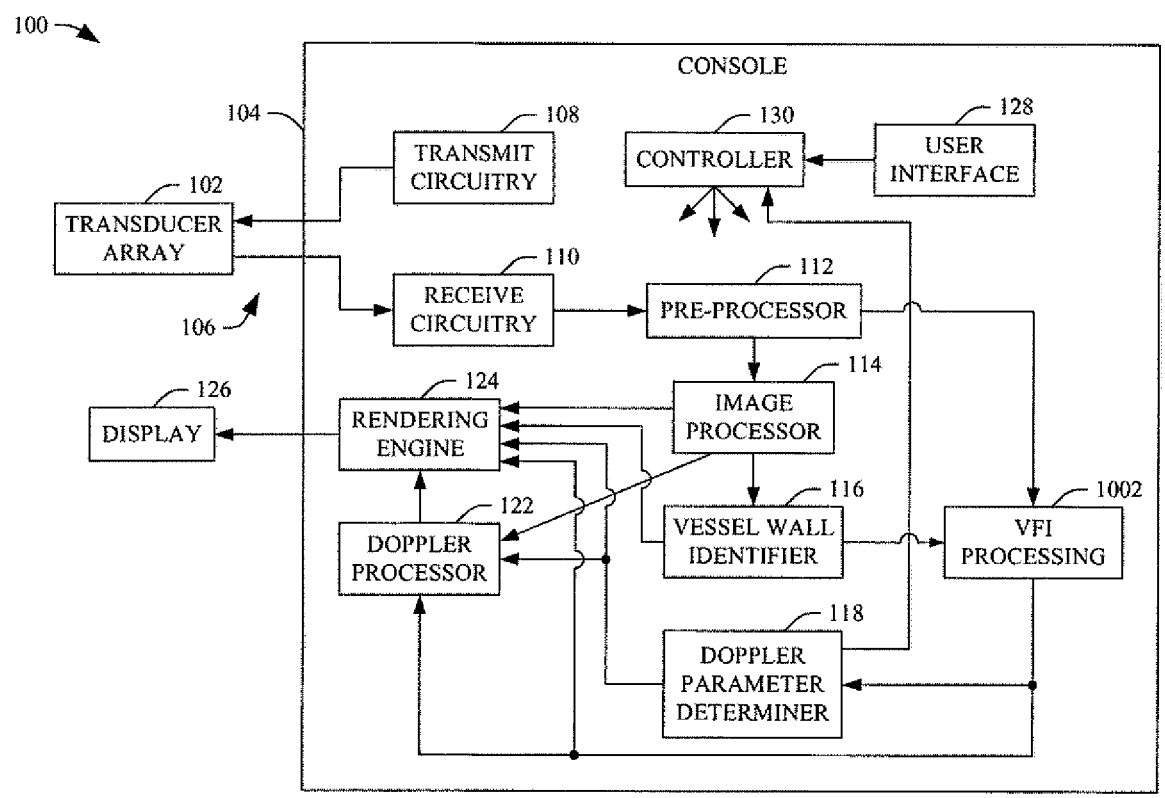
FIG. 10 shows a variation of the ultrasound imaging system with VFI processing.

A rendering engine 124 visually presents data via a display 126. FIG. 9 shows an example. In FIG. 9, the rendering engine 124 visually presents the B-mode image 600, the Doppler gate 608, graphical indicia 902 indicating the identified vessel walls 604/606, a velocity 904, a 2D spectrogram 906, an angle 908, a size of the sample volume 910, an indication of whether auto correction is on or off 912, and/or other information.

A user interface (UI) 128 includes one or more input devices (e.g., a button, a knob, a slider, a touch pad, a mouse, a trackball, a touch screen, etc.) and/or one or more output devices (e.g., a display screen, a light, an audio generator, etc.), which allow for interaction between a user and the ultrasound imaging system 100. By way of non-limiting example, the user interface (UI) 128 may include a feature to activate B-mode, Doppler mode, and/or other feature.

A controller 130 is configured to control one or more of the components of the console 104, the transducer array 102, and/or other device. For example, in one instance, the system controller 130 controls the transmit circuitry 108 and/or received circuitry 110 to control the transmit angles, transmit energies, transmit frequencies, transmit and/or receive delays, weights, etc. The system controller 130 also determines a frequency of the updates, including continuous steering, sample volume size setting and angle correction, triggered steering and/or setting the sample volume size, auto steering and/or setting the sample volume size (e.g., when the Doppler gate is moved), etc.

One or more of the components of the console 104 can be implemented via one or more processors (central processing unit (CPU), graphics processing unit (GPU), microprocessor, controller, etc.) executing one or more computer readable instructions encoded or embedded on computer readable storage medium, which is a non-transitory medium such as physical memory or other non-transitory medium, and excludes transitory medium. Additionally, or alternatively, at least one of the instructions can be carried by a carrier wave, a signal, or other transitory medium.

The ultrasound imaging system 100 can be part of a portable system on a stand with wheels, a system residing on a tabletop, and/or other system in which the transducer array 102 is housed in a probe or the like, and the console 104 is housed in an apparatus separate therefrom. In another instance, the transducer array 102 and the console 104 can be housed in a same apparatus such as within a single enclosure hand-held ultrasound scanning device.

Variations are discussed next.

In a variation, the system 100 is further configured for VFI processing 1002, as shown in FIG. 102. An example of VFI is described in patent application Ser. No. 13/838,329 to Bo Martins, U.S. Pat. No. 9,247,927, entitled "Doppler Ultrasound Imaging," and filed on Mar. 15, 2013, the entirety of which is incorporated herein by reference. In this variation, the B-mode image is used to identify the vessel wall, as described herein, for the VFI processing 1002, which can perform one or more of the function described in the '927 patent, e.g., determining the Doppler steering angle, sample size, and/or angle correction. As discussed above, identifying the vessel wall as described herein can decrease the time to determine flow direction and/or mitigate vessel wall uncertainty of VFI.

Figure 11:
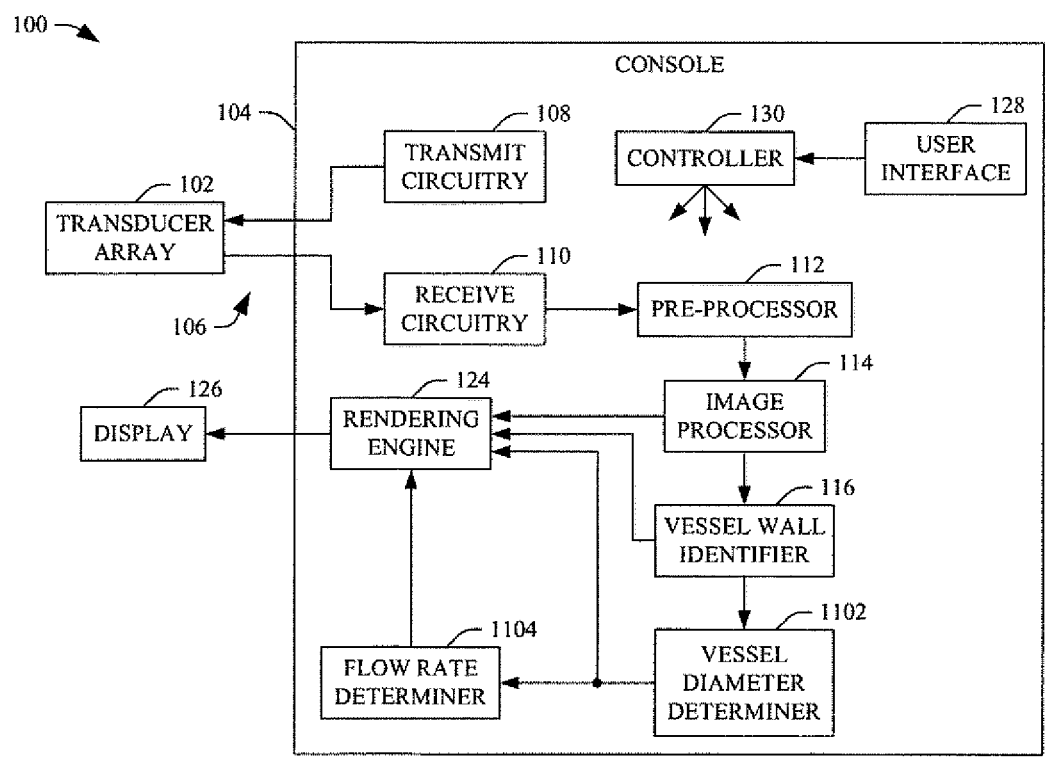
FIG. 11 shows a variation of the ultrasound imaging system with vessel diameter and flow rate determiners.

In another variation, the system 100 includes a vessel diameter determiner 1102 and flow rate determiner 1104, as shown in FIG. 11. The vessel diameter estimator 1102 uses the identified vessel wall to compute a vessel diameter. In one instance, this is achieved by extending a line perpendicular to a center of the gate respectively to opposing walls, and measuring the distance between the walls. The flow rate determiner 1104 can determine a flow rate based on this diameter. This can be achieved by opening the Doppler gate to encompass the entire vessel based on the identified walls and measuring the flow through the gate. The vessel diameter can additionally or alternatively be used to determine other information.

In general, the volume flow rate specifies the amount of blood cells pass through predetermined region of a blood vessel per time unit (e.g., in units of ml/min). Volume flow rate can be computed using an angle-corrected velocity of the blood cells passing through the opening of the Doppler gate multiplied with the area of a cross-section of the vessel, which is determined based on a diameter determined from the location of the inner vessel wall. Because the diameter estimate does not depend on color gain, a more robust estimate of volume flow rate can be achieved than what it is possible with VFI data alone. Automatic measurements of volume flow rate in peripheral vessels, the abdomen, and/or other anatomical region are now also possible.

Figure 12:
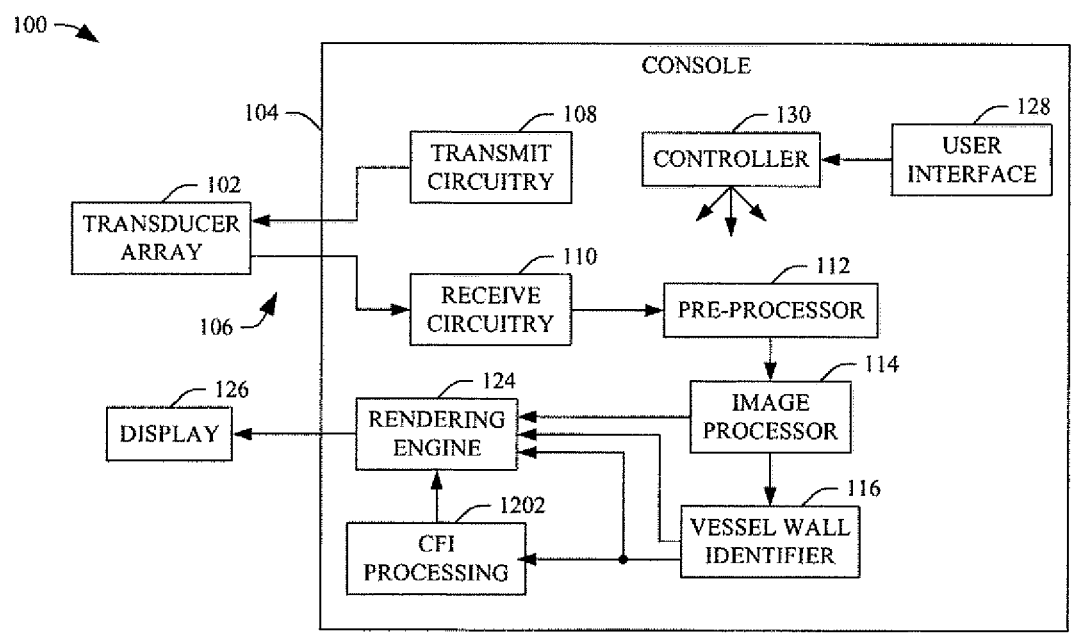
FIG. 12 shows a variation of the ultrasound imaging system with color flow imaging processing.

In another variation, the system 100 includes color flow imaging (CFI) processing 1202, as shown in FIG. 12. In general, too much color gain fills the entire color box and does not reflect the flow, and too little will make it difficult to see the flow. With this variation, the outline of the vessel is used to detect mirroring in the distal vessel wall and eliminate distal blooming of color. For this, the vessel is segmented using the outline. Then, for a plurality of different color gain settings, a correlation with the B-image is determined, and the color gain with the best correlation with the B-image is automatically selected. Maps are generated by assigning a value of "0" to no color regions (no vessel) and a value of "1" to color regions (vessel). A detection threshold of presence of color flow can be adjusted to ensure maximum correlation with the B-mode image, thereby providing a key for automatic color gain adjustment.

Another variation includes a combination of FIGS. 1, 10, 11, 12 and/or other configuration.

Figure 13:
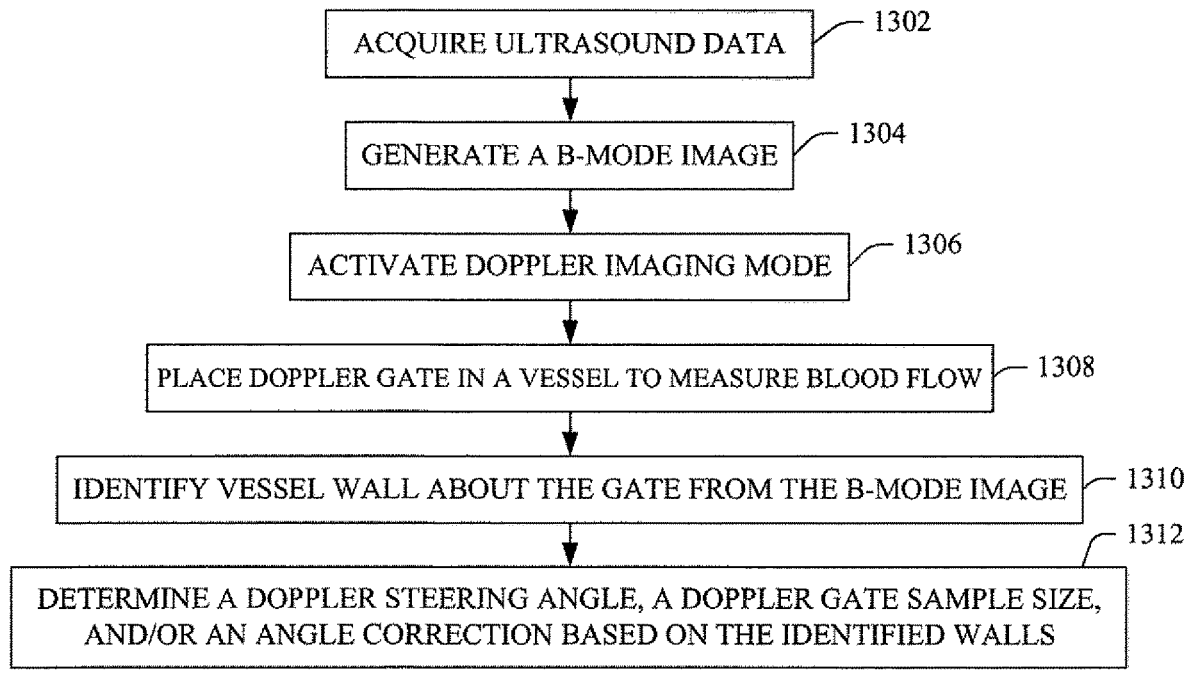
FIG. 13 illustrates an example method in accordance with an embodiment herein.

FIG. 13 illustrates an example method in accordance with an embodiment herein.

It is to be understood that the following acts are provided for explanatory purposes and are not limiting. As such, one or more of the acts may be omitted, one or more acts may be added, one or more acts may occur in a different order (including simultaneously with another act), etc.

At 1302, ultrasound data is acquired with an ultrasound imaging transducer.

At 1304, a B-mode image is generated from the acquired ultrasound data.

At 1306, Doppler mode is activated.

At 1308, a Doppler gate is placed in a vessel of interest.

At 1310, vessel walls of the vessel of interest are identified from the B-mode image, as described herein and/or otherwise.

At 1312, one or more of a Doppler steering angle, a Doppler gate sample size, or Doppler angle correction is determined based on the identified walls.

Figure 14:
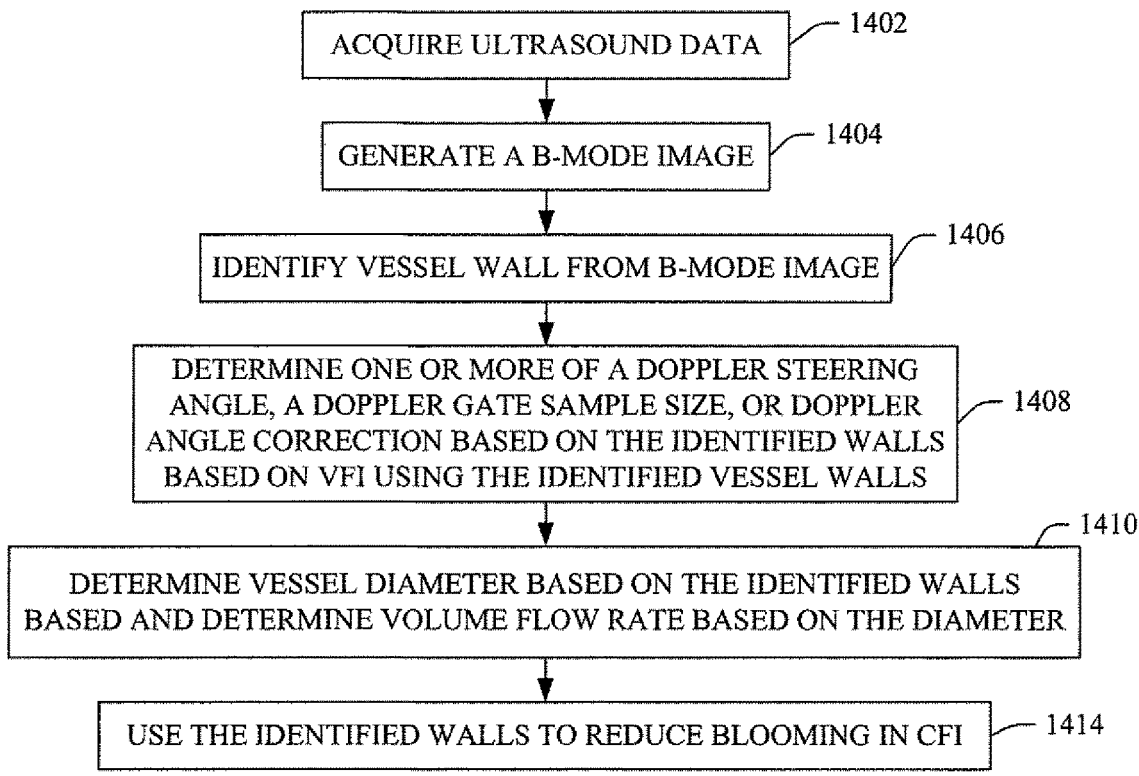
FIG. 14 illustrates another example method in accordance with an embodiment herein.

FIG. 14 illustrates another example method in accordance with an embodiment herein.

It is to be understood that the following acts are provided for explanatory purposes and are not limiting. As such, one or more of the acts may be omitted, one or more acts may be added, one or more acts may occur in a different order (including simultaneously with another act), etc.

At 1402, ultrasound data is acquired with an ultrasound imaging transducer.

At 1404, a B-mode image is generated from the acquired ultrasound data.

At 1406, vessel walls of the vessel of interest are identified from the B-mode image, as described herein and/or otherwise.

At 1408, one or more of a Doppler steering angle, a Doppler gate sample size, or Doppler angle correction is determined based on VFI using the identified walls. In a variation, act 1408 is omitted.

At 1410, a vessel diameter is determined from the identified walls and a volume flow rate is determined from the diameter. In a variation, act 1408 is omitted.

At 1412, the identified walls are used to reduce blooming in CFI. In a variation, act 1408 is omitted.

The methods described herein may be implemented via one or more processors executing one or more computer readable instructions encoded or embodied on computer readable storage medium such as physical memory (and excluding transitory memory) which causes the one or more processors to carry out the various acts and/or other functions and/or acts. Additionally or alternatively, the one or more processors can execute instructions carried by transitory medium such as a signal or carrier wave.

Although the above is discussed in connection with blood cells flowing through a blood vessel, it is to be understood that the above also applies to other structure flowing through other tubular objects.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   receive circuitry configured to receive electrical signals from ultrasound transducer elements, wherein the electrical signals are indicative of sensed ultrasound echo signals, including echo signals from a vessel;
   a pre-processor configured to digitize the electrical signals and to process samples of the digitized electrical signals to detect envelope values and output signals of samples of envelope values;
   an image processor configured to process the signals of samples of envelope values and generate a B-mode image that includes the vessel;
   a vessel wall identifier configured to generate in image of mirror strength values corresponding to the pixels in the B-mode image, wherein the vessel wall identifier is configured to, for each pixel in the B-mode image values:
     weight a first set of samples of the signal of envelope values with a first set of weights, thereby generating a first weighted signal, wherein the first set of weights has a first length;
     weight a second set of samples of the signal of envelope values with a second set of weights, thereby generating a second weighted signal, wherein the second set of weights has the first length,
     wherein the first set of samples and the second set of samples are separated by one or more samples of the signal of envelope values;
     subtract the samples of the second weighted signal from corresponding samples of the first weighted signal generating a weighted sum of samples having a length of the first length plus one
     generate a mirroring strength value by dividing the weighted sum by the first length;

wherein the vessel wall identifier is further configured to subtract the image of mirroring strength values from the B-mode image and threshold a result of the subtraction to generate a fluid mask out echo tissue signal inside the vessel with a predetermined threshold value.

2. The system of claim 1, further comprising:
a Doppler parameter determiner configured to determine a flow direction in the vessel based on a doppler gate in the vessel and at least one of a proximal wall and a distal wall of the vessel.

3. The system of claim 2, wherein the flow direction is in a direction of at least one of the proximal and distal walls.

4. The system of claim 2, wherein the Doppler parameter determiner fits a line to at least one of the proximal and distal walls, wherein the flow direction is in a direction of the fitted line.

5. The system of claim 2, wherein the flow direction is in a direction of a sub-portion of one of the proximal and distal walls.

6. The system of claim 2, wherein the Doppler parameter determiner identifies the proximal and distal walls from a current frame.

7. The system of claim 2, wherein the Doppler parameter determiner identifies the proximal and distal walls based on an average over multiple frames.

8. The system of claim 2, wherein the Doppler parameter determiner determines a Doppler steering angle between an ultrasound beam direction and the flow direction.

9. The system of claim 2, wherein the Doppler parameter determiner determines an angle correction based on the flow direction.

10. The system of claim 2, wherein the Doppler parameter determiner determines the Doppler gate sample volume based on the identified proximal and distal walls.

11. The system of claim 1, further comprising:
a vector flow imaging processor configured to determine one or more of a Doppler steering angle, a Doppler gate sample volume and angle correction from the proximal and distal walls of the vessel.

12. The system of claim 1, further comprising:
a vessel diameter determiner configured to determine a diameter of the vessel based on the proximal and distal walls.

13. The system of claim 12, further comprising:
a flow rate determiner that determines a volume flow rate parameter value for flowing structure within the Doppler gate based on the vessel diameter.

14. The system of claim 1, further comprising:
color flow imaging processor configured to eliminate distal blooming of color based on an outline of the proximal and distal walls of the vessel.

15. The system of claim 14, wherein the color flow imaging processor is further configured to:
segment the vessel;
determine a correlation with the B-image for a plurality of different color gain settings; and
automatically select a color gain with a best correlation with the B-image.

16. The system of claim 15, wherein the color flow imaging processor is further configured to:
generate a map by assigning a value of zero to no color regions which indicate no vessel and a value of one to color regions which indicate vessel; and
adjust a detection threshold of presence of color flow for a maximum correlation with the B-mode image.

17. The system of claim 1, wherein the vessel wall identifier is further configured to:
overlay a graphical representation over at least one of a proximal and a distal wall of the vessel.

18. The system of claim 1, wherein the vessel wall identifier is further configured to:
subtract an offset from the mirroring strength values for near field imaging.

19. The system of claim 18, wherein the offset is decreased monotonically from a constant value at a probe surface acquiring the echo signals to zero at a predetermined sample depth.

20. The system of claim 1, wherein a sum of the weights of the weight sum equals zero.

* * * * *